US006780836B2

(12) United States Patent
Unemori

(10) Patent No.: US 6,780,836 B2
(45) Date of Patent: Aug. 24, 2004

(54) METHOD OF PROMOTING ANGIOGENESIS USING RELAXIN

(75) Inventor: Elaine Unemori, Oakland, CA (US)

(73) Assignee: BAS Medical, Inc., San Mateo, CA (US)

( * ) Notice: Subject to any disclaimer, the term of this patent is extended or adjusted under 35 U.S.C. 154(b) by 0 days.

(21) Appl. No.: 09/780,758

(22) Filed: Feb. 8, 2001

(65) Prior Publication Data

US 2001/0018418 A1 Aug. 30, 2001

Related U.S. Application Data

(63) Continuation of application No. 08/698,359, filed on Aug. 15, 1996, now Pat. No. 6,211,147
(60) Provisional application No. 60/002,355, filed on Aug. 15, 1995.

(51) Int. Cl.[7] ............................................... A61K 38/30
(52) U.S. Cl. ....................... 512/12; 435/69.1; 530/399
(58) Field of Search ..................... 514/2, 12; 435/69.1; 530/399

(56) References Cited

U.S. PATENT DOCUMENTS

| | | | |
|---|---|---|---|
| 5,023,088 A | * | 6/1991 | Wong et al. |
| 5,023,321 A | | 6/1991 | Hudson et al. |
| 5,166,191 A | * | 11/1992 | Cronin et al. |
| 5,451,572 A | | 9/1995 | Cipolla et al. |
| 5,464,756 A | | 11/1995 | Henner et al. |
| 5,478,807 A | * | 12/1995 | Cronin et al. |
| 5,753,623 A | | 5/1998 | Amento et al. |
| 5,811,395 A | | 9/1998 | Schwabe et al. |
| 5,911,997 A | | 6/1999 | Schwabe et al. |
| 5,952,296 A | | 9/1999 | Bigazzi |

FOREIGN PATENT DOCUMENTS

WO      WO 90/11760      10/1990

OTHER PUBLICATIONS

Asahara et al., 1995, "Local Delivery of Vascular Endothelial Growth Factor Accelerates Reendothelialization and Attenuates Intimal Hyperplasia in Balloon–Injured Rat Carotid Artery," Circulation, vol. 91:2793–2801.
Breece et al., U.S. patent Ser. No. 08/080,354, filed Jun. 21, 1992.
Bryant–Greenwood (1982) "Relaxin as a new hormone," Endocrine Reviews, vol. 3:62–90.
Casten et al. "Use of relaxin in the treatment of scleroderma," J. Am. Med. Assoc., vol. 166:319–324.
Claffey et al. (1992) "Vascular endothelial growth factor. Regulation by cell differentiation and activated second messenger pathways," J. Biol. Chem., vol. 267:16317–16322.
Dallenbach–Hellwag et al. (1966) "The Effect of Relaxin on the Endometrium of Monkeys," American Journal of Anatomy, vol. 119:61–78.
Garrido et al. (1993) "Transcriptional regulation of vascular endothelial growth factor gene expression in ovarian bovine granulosa cells," Growth Factors, vol. 8: 1 09–1 1 7.
Guyto. Textbook of Medical Physiology, 8th ed., WB Saunders Comp., Philadelphia, p. 527.
Hisaw et al. (1967) "Effects of Relaxin on the Endothelium of Endometrial Blood Vessels in Monkeys," Endocrinology, vol. 81:375–385.
Hisaw (1926) Proc. Soc. Exp. Biol. Med. 23:661–663.
James et at. (1977) "Primary structure of porcine relaxin: homology with insulin and related growth factors," Nature, vol. 267:544–546.
Norrby et al. (1996) "Relaxin, a potent microcirculatory effector, is not angiogenic," International Journal of Microcirculation: Clinical and Experimental, vol. 16(5): 227–31.
Phillips etal. (1990) "Vascular endothelial growth factor is expressed in rat corpus luteum," Endocrinology 127:965–967.
Prusiner, Prior Biology (Abstract). In: Prion Dis. Hum. Anim., Horwood Pub., London, p. 533–567.
Schwabe et al., U.S. patent application Ser. 08/483,476, filed Jun. 7, 1995.
Schwabe et al., U.S. patent application Ser. 08/484,219, filed Jun. 7, 1996.
Sharkey etal (1993) J. Reprod. Pert. 99:609–615.
Shima et al. (1995) "Hypoxic induction of endothelial cell growth factors in retinal cells: Identification and characterization of vascular endothelial growth factor (VEGF) as the mitogen" Mol. Med , 1(2): 182–193.
Takeshita et al. (1995) "Time Course of Increased Cellular Proliferation in Collateral Arteries after Administration of Vascular Endothelial Growth Factor in a Rabbit Model of Lower Limb Vascular Insufficiency," American Journal of Pathology, 147:1649–1660.
Thomas (1996) "Vascular endothelial growth factor, a potent and selective angiogenic agent," J. Biol. Chem., vol. 271:603–606.
Torry et al. (1995) "Vascular Endothelial Growth Factor Expression in Transplanted Human Hearts", Transplantation 12:1451–1457.
Unemori et al. (1993) "Human relaxin decreases collagen accumulation in vivo in two rodent models of fibrosis," J. Invest. Dermatol., 101(3): 280–285.
Unemori et al. (1996) "Relaxin Causes Secretion of Vascular Endothelial Growth Factor (VEGF) by a Human Monocytic Cell Line In Vitro and Stimulates Angiogenesis in a Murine Model In Vivo," Wound Repair and Regeneration 4:A179.
Unemori et al. (1996) "Regulation of Angiogenesis by Relaxin: Possible Mediation by Vascular Endothelial Growth Factor Induction in Monocytes," J. investigative Medicine 44:31 5 A.
Weiss (1984) "Relaxin," Ann. Rev. Physiol., vol. 46:43–52.

* cited by examiner

Primary Examiner—Lorraine Spector
Assistant Examiner—Claire M. Kaufman
(74) Attorney, Agent, or Firm—Karl Bozicevic; Paula A. Borden; Bozicevic, Field & Francis, LLP

(57) ABSTRACT

Relaxin is useful for promoting angiogenesis and the treatment of infections or ischemic wounds where the injury results from lack of oxygen due to poor circulation.

7 Claims, No Drawings

METHOD OF PROMOTING ANGIOGENESIS USING RELAXIN

CROSS-REFERENCE TO RELATED APPLICATIONS

This application is a continuation of application Ser. No. 08/698,359, filed Aug. 15, 1996 now U.S. Pat. No. 6,211,147 of which is incorporated herein by reference and to which is claimed priority under 35 U.S.C. §120.

RELATED APPLICATION

This application is a continuation-in-part of U.S. Provisional Application Ser. No. 60/002,355, filed Aug. 15, 1995.

FIELD OF THE INVENTION

The present invention relates to the treatment of ischemic wounds, for example, where the injury results from lack of oxygen due to poor circulation such as in the diseases diabetes, scleroderma, and the like, by the administration of relaxin. The present invention also relates to the promotion of angiogenesis.

BACKGROUND INFORMATION

Mature human relaxin is a hormonal peptide of approximately 6000 daltons known to be responsible for remodelling the reproductive tract before parturition, thus facilitating the birth process. This protein appears to modulate the restructuring of connective tissues in target organs to obtain the required changes in organ structure during pregnancy and parturition. See, Hisaw, F. L., Proc. Soc. Exp. Biol. Med., 23: 661–663 (1926); Schwabe, C., et al., Biochem. Biophys. Res. Comm., 75: 503–570 (1977); James, R. et al., Nature, 267: 544–546 (1977). A concise review of relaxin was provided by Sherwood, D. in *The Physiology of Reproduction*, Chapter 16, "Relaxin", Knobil, E. and Neill, J., et al. (eds.), (Raven Press Ltd., New York), pp. 585–673 (1988). Circulating levels of relaxin are elevated for the entire nine months of pregnancy and drop quickly following delivery.

While predominantly a hormone of pregnancy, relaxin has also been detected in the non-pregnant female as well as in the male. Bryant-Greenwood, G. D., Endocrine Reviews, 3: 62–90 (1982) and Weiss, G., Ann. Rev. Physiol., 46:43–52 (1984).

Relaxin has been purified from a variety of species including porcine, murine, equine, shark, tiger, rat, dogfish and human, and shows at least primary and secondary structural homology to insulin and the insulin-like growth factor. In the human, relaxin is found in most abundance in the corpora lutea (CL) of pregnancy. However, specific nuclei in the brain have relaxin receptors and other nuclei contain messenger RNA for relaxin. Several nuclei with cells bearing relaxin receptors are found in the area of the hypothalamus.

Two human gene forms have been identified, (H1) and (H2). Hudson, P., et al., Nature, 301: 628–631 (1983); Hudson, P., et al., The EMBO Journal, 3: 2333–2339 (1984); and U.S. Pat. Nos. 4,758,516 and 4,871,670. Only one of the gene forms (H2) has been found to be transcribed in CL. It remains unclear whether the (H1) form is expressed at another tissue site, or whether it represents a pseudo-gene. When synthetic human relaxin (H2) and certain human relaxin analogs were tested for biological activity, the tests revealed a relaxin core necessary for biological activity as well as certain amino acid substitutions for methionine that did not affect biological activity. Johnston, et al., in *Peptides: Structure and Function, Proc. Ninth American Peptide Symposium*, Deber, C. M., et al. (eds.) (Pierce Chem. Co. 1985).

Methods of making relaxin are also described in U.S. Pat. No. 4,835,251 and in co-pending U.S. Ser. Nos. 07/908,766 (PCT US90/02085) and 08/080,354 (PCT US94/0699). Methods of using relaxin in cardiovascular therapy and in the treatment of neurodegenerative diseases are described in U.S. Pat. No. 5,166,191 and in U.S. Ser. No. 07/902,637 (PCT US92/06927). Certain formulations of human relaxin are described in allowed U.S. Ser. No. 08/050,745.

Recombinant human relaxin (H2) in currently in Phase I human clinical trials in scleroderma patients. Scleroderma is a disease involving an imbalance in tissue reformation giving rise to the overproduction of collagen, and ultimately resulting in swelling and hardening of the skin (and affected organs).

Vascular Endothelial Growth Factor (VEGF) has also been localized in situ in the corpus luteum (CL) of pregnancy, as well as the placenta and the endometrium. See Sharkey et al., J. Reprod. Fert. 99:609–615 (1993); Li et al. Growth Factors 22:277–282 (1994); Phillips et al. Endocrinology 127:965–967 (1990). VEGF, highly conserved glycoprotein secreted by macrophages, exhibits a potent ability to induce new vessel growth in vivo. VEGF is mitogen specific for endothelial cells and can induce both endothelial cell migration and serine and metalloproteinase expression (for review, see Thomas, K. A., J. Biol. Chem. 271:603–606 (1996). The strongest sites of VEGF expression are the fetal and maternal macrophages. Besides its proposed role in promoting new vessel growth during pregnancy, VEGF has also been proposed to be involved in persistent and dysregulated vessel growth in pathological conditions such as tumor metastasis, diabetic retinopathy, and rheumatoid arthritis.

SUMMARY OF THE INVENTION

In one aspect, the invention relates to a method of promoting angiogenesis in a mammal in need thereof by administering a therapeutically effective amount of relaxin. In a preferred embodiment, relaxin is administered in an amount sufficient to maintain a serum concentration of at least about 1 ng/ml. In a further preferred embodiment the relaxin is recombinant human relaxin (H2).

In another aspect, the invention relates to the treatment of infections or ischemic wounds by administering a therapeutically effective amount of relaxin. In a particularly preferred embodiment, the infection or ischemic wound is one where injury has resulted from lack of oxygen due to poor circulation.

In yet another aspect of the invention, there is provided a method of using relaxin for the manufacture of a medicant for the treatment of an infection or ischemic wound, or for the manufacture of a medicant for the promotion of angiogenesis. In preferred versions of these embodiments, the relaxin is recombinant human relaxin (H2).

DETAILED DESCRIPTION OF THE INVENTION

Definitions and General Parameters

As used in the present specification, the following words and phrases are generally intended to have the meanings as set forth below, except to the extent that the context in which they are used indicates otherwise.

"Optional" or "optionally" means that the subsequently described event or circumstance may or may not occur, and that the description includes instances where said event or circumstance occurs and instances in which it does not.

The term "treatment" or "treating" means any therapeutic intervention in a mammal, including:

(i) prevention, that is, causing the clinical symptoms not to develop;

(ii) inhibition, that is, arresting the development of clinical symptoms; and/or (iii) relief, that is, causing the regression of clinical symptoms.

The term "effective amount" means a dosage sufficient to provide treatment for the disease state being treated. This will vary depending on the patient, the disease and the treatment being effected.

The term "relaxin" means human relaxin, including intact full length relaxin or a portion of the relaxin molecule that retains biological activity [as described in U.S. Pat. No. 5,023,321, preferably recombinant human relaxin (H2)] and other active agents with relaxin-like activity, such as Relaxin Like Factor (as described in U.S. Pat. No. 5,911,997 at SEQ ID NOS: 3 and 4, and column 5, line 27-column 6, line 4), relaxin and portions that retain biological activity analogs and portions that retain biological activity (as described in U.S. Pat. No. 5,811,395 at SEQ ID NOS: 1 and 2, and column 3, lines 16–40), and agents that competitively displace bound relaxin from a receptor. Relaxin can be made by any method known to those skilled in the art, preferably as described in U.S. Pat. No. 4,835,251 and in co-pending U.S. Ser. Nos. 07/908,766 (PCT US90/02085) and 08/080,354 (PCT US94/0699).

The Role of Relaxin Promoting Angiogenesis

The invention is based, in part, on the surprising discovery that relaxin promotes angiogenesis in an in vivo assay, as described more fully below by way of working examples. Specifically, relaxin was found angiogenic in both a rabbit corneal injection protocol and by the matrigel subcutaneous insert vascularization protocol.

Also reported herein is the novel discovery that relaxin induces secretion of a potent angiogenic factor, Vascular Endothelial Growth Factor ("VEGF"), in the monocyte-like cell line THP-1. This finding further broadens the scope of relaxin's known biological activity. Since macrophages are known to play a key role in angiogenesis, both during and outside of pregnancy, relaxin's potential regulatory role straddles both.

In the THP-1 cell line, relaxin stimulates the expression of at least 3 of the 4 isoforms of VEGF: the 121, the 165, and the 189 amino acid isoforms. Although all forms are reportedly bioactive, the 121 and 165 amino acid forms are secreted while the larger molecules remain associated with the extracellular matrix unless enzymatically released. This stimulation of relaxin expression occurred at the transcriptional level, even in the presence of cycloheximide, indicating that no de novo protein synthesis was required. Additionally, results presented herein indicate that the induction of VEGF by relaxin in THP-1 cells may be mediated by cAMP and protein kinase C. This finding is consistent with the known role of cAMP in the stimulation of VEGF expression in other cell types. See, for example, Claffey et al., J. Biol. Chem. 267:16317–16322 (1992), and Garrido et al., Growth Factors 8:109–117 (1993). The rapid increase in VEGF transcripts following relaxin treatment of THP-1 cells is similar to that seen in preadipocytes following forskolin stimulation (Garrido et al., supra). Indeed, the rapidity of the induction and the lack of cycloheximide effect may suggest a pathway common to THP-1 cells and preadipocytes.

Utility, Testing and Administration

Utility

Relaxin is useful for promoting angiogenesis and treating infections and ischemic wounds (e.g., poorly healing ischemic ulcers) characteristic of diseases, such as diabetes and scleroderma, involving poorly vascularized disease sites and macrophage associated inflammation. Macrophages are one of the most important sources of angiogenic factors. It has surprisingly been discovered that certain macrophage lines contain relaxin binding sites. It has also surprisingly been discovered that relaxin promotes angiogenesis in vivo.

Testing

In vitro activity for relaxin binding to macrophages is determined using $p^{32}$ labeled relaxin binding sites.

In vivo activity for angiogenesis is determined by the rabbit corneal injection protocol and by the matrigel subcutaneous insert vascularization protocol.

Administration

Relaxin is administered at a therapeutically effective dosage, e.g., a dosage sufficient to promote angiogenesis and/or provide treatment for the above-referenced disease states.

Administration of relaxin can be via any of the accepted modes of administration for agents that serve similar utilities, preferably by systemic administration.

While human dosage levels for promoting angiogenesis have yet to be optimized for relaxin, generally, a daily dose is from about 0.1 to 500.0 μg/kg of body weight per day, preferably about 6.0 to 200.0 μg/kg, and most preferably about 12.0 to 100.0 μg/kg. Generally it is sought to obtain a serum concentration of relaxin approximating or greater than normal circulating levels in pregnancy, i.e., 1.0 ng/ml, such as 0.5 to 50 ng/ml, preferably 1.0 to 20 ng/ml. In the ongoing clinical trials, dosages of about 6.0 μg/kg, 12.0 g/kg and 50 μg/kg have respectively resulted in serum concentrations of about 1.8 ng/ml±0.3, 3.6 ng/ml±0.6, and 11.8 ng/ml±1.6. Thus, for administration to a 70 kg person, the dosage range would be about 7.0 μg to 3.5 mg per day, preferably about 42.0 μg to 2.1 mg per day, and most preferably about 84.0 to 700.0 μg per day. The amount of relaxin administered will, of course, be dependent on the subject and the severity of the affliction, the manner and schedule of administration and the judgment of the prescribing physician.

In employing relaxin for treatment of the above conditions, any pharmaceutically acceptable mode of administration can be used. Relaxin can be administered either alone or in combination with other pharmaceutically acceptable excipients, including solid, semi-solid, liquid or aerosol dosage forms, such as, for example, tablets, capsules, powders, liquids, gels, suspensions, suppositories, aerosols or the like. Relaxin can also be administered in sustained or controlled release dosage forms (e.g., employing a slow release bioerodable delivery system), including depot injections, osmotic pumps (such as the Alzet implant made by Alza), pills, transdermal and transcutaneous (including electrotransport) patches, and the like, for prolonged administration at a predetermined rate, preferably in unit dosage forms suitable for single administration of precise dosages. The compositions will typically include a conventional pharmaceutical carrier or excipient and relaxin. In addition, these compositions may include other active agents, carriers, adjuvants, etc. Generally, depending on the intended mode of administration, the pharmaceutically acceptable composition will contain about 0.1% to 90%, preferably about 0.5% to 50%, by weight of relaxin, the remainder being suitable pharmaceutical excipients, carriers, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The formulations of human relaxin described in U.S. Ser. No. 08/050,745 are particularly preferred.

Parenteral administration is generally characterized by injection, either subcutaneously, intradermally, intramuscularly or intravenously, preferably subcutaneously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, and the like.

The percentage of relaxin contained in such parenteral compositions is highly dependent on the specific nature thereof, as well as the needs of the subject. However, percentages of active ingredient of 0.01% to 10% in solution are employable, and will be higher if the composition is a solid which will be subsequently diluted to the above percentages. Preferably the composition will comprise 0.2–2% of the relaxin in solution.

A more recently devised approach for parenteral administration employs the implantation of a slow-release or sustained-release system, such that a constant level of dosage is maintained. Various matrices (e.g., polymers, hydrophilic gels, and the like) for controlling the sustained release, and for progressively diminishing the rate of release of active agents such as relaxin are known in the art. See, U.S. Pat. No. 3,845,770 (describing elementary osmotic pumps); U.S. Pat. Nos. 3,995,651, 4,034,756 and 4,111,202 (describing miniature osmotic pumps); U.S. Pat. Nos. 4,320,759 and 4,449,983 (describing multichamber osmotic systems referred to as push-pull and push-melt osmotic pumps); and U.S. Pat. No. 5,023,088 (describing osmotic pumps patterned for the sequentially timed dispensing of various dosage units).

Formulations of relaxin may also be administered to the respiratory tract as a nasal or pulmonary inhalation aerosol or solution for a nebulizer, or as a microfine powder for insufflation, alone or in combination with an inert carrier such as lactose, or with other pharmaceutically acceptable excipients. In such a case, the particles of the formulation may advantageously have diameters of less than 50 microns, preferably less than 10 microns. See, e.g., U.S. Pat. No. 5,364,838, which discloses a method of administration for insulin that can be adapted for the administration of relaxin in the present invention.

EXAMPLES

The following examples are given to enable those skilled in the art to more clearly understand and to practice the present invention. They should not be considered as limiting the scope of the invention, but merely as being illustrative and representative thereof.

EXAMPLE 1

Rabbit Corneal Assay

Test and control material is mixed with hydron into a 0.1 cc disc (resembling a small contact lens). The disc is implanted into a rabbit corneal stroma micro pocket using appropriate anesthesia for the procedure. After one week, neo-capillary growth toward the disc is measured and scored (0–4) utilizing a standard anatomic grading scale. A score of 0 means no growth. A score of 1 means capillaries (one or two) just entering the corneal stroma from the limbus toward the pocket. A score of 3 means vessels have grown to the base of the implant. A score of 4 means vessels have grown around the implant.

By following the above-described procedure testing sixteen blinded samples, one corneal vitreous was punctured and 15 scores were obtained. Mean placebo score (n=7) was 0.6 with a standard error of 0.3 while the mean relaxin score (n=8) was 1.5 with a standard error of 0.5. P value was 0.08.

In conclusion, relaxin was angiogenic when tested in this assay.

EXAMPLE 2

Murine Matrigel Assay

Matrigel (Collaborative Biomedical, Bedford, Mass.) is a reconstituted basement membrane complex containing primarily laminin and type IV collagen. It is isolated from the Engelbreth-Holm-Swarm (EHS) murine tumor. At room temperature, matrigel is liquid; but when injected subcutaneously into a mouse it reconstitutes as a gel.

Test substance is mixed with matrigel (1% v/v media in 1 cc matrigel) at room temperature and then injected subcutaneously into a mouse dorsum (5 month old female Swiss-Webster). After one week, the mouse is sacrificed and the gel plug(s) harvested. Samples are fixed in buffered formalin, paraffin embedded, sectioned (4 $\mu$) and H&E stained. The samples are scored 1 (positive), 0.5 (indeterminate) or 0 (negative).

Relaxin, when tested as described above, caused endothelial cells (confirmed with factor VIII staining) to migrate into the gel, organize linear structures, and form vessels with blood cells as compared with non-supplemented control gel plugs, which supported no endothelial cell infiltration. Sixteen blinded samples were tested. Sixteen scores were obtained. The mean control score (n=8) was 0.3 with a standard error of 0.1. The mean relaxin score was 0.8 with a standard error of 0.1. P value was 0.02.

In conclusion, relaxin was angiogenic when tested in this assay.

EXAMPLE 3

Effect of Relaxin on VEGF Production in THP-1 Cells

A cell line derived from the peripheral blood cells of a 1 year old male with leukemia which has been described as monoblast or immature monocytes, THP-1, was chosen for studying the effect of relaxin on cultured cells. THP-1 cells (ATCC# TIB202) were grown in Iscove's medium supplemented with 10% fetal bovine serum and 2 mM L-glutamine. For experiments, THP-1 cells were cultured at $5\times10^5$ cells/ml in 24 well plates and incubated at 37° C. with 20% $O_2$ and 5% $CO_2$. Cells were treated with recombinant human relaxin (H2) in 10 mM citrate, pH 5.0 at doses ranging from 0.04–50 ng/ml, or with diluent alone, for 8 hours. Conditioned media and cells were then collected, and cells removed by centrifugation at 500 g for 5 minutes. VEGF protein secretion was quantified in an ELISA kit (R & D Systems, Minneapolis, Minn.).

Relaxin caused no observable morphological changes, such as adherence to plastic or clumping, in THP-1 cells, nor did it influence thymidine uptake, metalloproteinase expression patterns, or nitric oxide production. However, relaxin was shown to induce VEGF protein secretion is a dose dependent manner, peaking at 1 ng/ml relaxin.

A time-course study of expression following treatment with 1 ng/ml and 100 ng/ml relaxin demonstrated that VEGF increased in the conditioned media in roughly linear fashion up to at least 72 hours.

This same assay was used to compare the effect of other members of the relaxin family, specifically insulin, IGF-I, and IGF-II (Promega, Madison, Wis.), on VEGF induction at equivalent molar concentrations (17 nM). Neither IGF-I and IGF-II induced VEGF production. However, insulin stimulated a small but significant amount of VEGF expression, roughly 30% of that induced by relaxin.

Because estrogen treatment appears to upregulate binding of relaxin to some cell types, THP-1 cells were treated with 1 $\mu$M 17-$\beta$-estradiol simultaneously with relaxin, or pretreated for 48 hours prior to relaxin addition. Neither treatment protocol resulted in a difference in VEGF stimulation when compared to relaxin treatment alone.

Thus, the results showed that relaxin induces VEGF secretion in THP-1 cells in a dose dependent fashion which is independent of the effects of estrogen.

EXAMPLE 4

Relaxin Regulation of VEGF Transcription

In order to determine whether relaxin-induced increases in VEGF protein were reflected at the transcript level and to characterize VEGF isoform regulation, PCR analysis of steady state VEGF mRNA was performed. Total RNA was extracted from $10^6$ THP-1 cells following a 2 hour treatment with recombinant human relaxin (H2) (10 ng/ml) using RNAzol (Tel-Test, Tex.), according to the manufacturer's instructions. Primers designed to amplify and distinguish among all four VEGF isoforms were used: 5'-CCA TGA ACT TTC TGC CCT-3' (sense) (SEQ ID NO: 1) and 5'-TGC ATC GTT CTG TAT CAG TCT-3' (antisense) (SEQ ID NO: 2). These primers spanned the gene from exon 1 to exon 8 and generated 4 different product sizes based on the number of exons spliced out during mRNA processing. A product size of 520 bp indicates the presence of the VEGF121 transcript, a size of 650 bp corresponds to VEGF165, a 730 bp band to VEGF189, and a 780 bp band to VEGF206. 0.7 $\mu$M of each primer was used in a reaction mixture with 2.5 U Taq polymerase. Samples were denatured at 95° C. for 30s, annealed at 60° C. for 30s, and extension performed at 72° C. for 30s. Amplification occurred over 30 cycles.

PCR products were size-fractionated on a 1.5% agarose gel and stained with ethidium bromide. The gel results showed that recombinant human relaxin (H2) increased the levels of expression of three bands corresponding to VEGF121, 165, and 189. The increase was detectable at 30 minutes, and was roughly 2-fold by 2 hours. The addition of cycloheximide did not interfere with or amplify this increase, indicating that de novo protein synthesis is not involved in this effect.

Southern blot analysis of the PCR products was then performed using probes that distinguish among the transcripts. The gel-fractionated PCR products were transferred to Genescreen and probed with $^{32}$P-end labelled probes specific to sequences within exons 4, 6, and 7. Probes designed as follows: Ex4: 5'-TTC CTA CAG CAC AAC AAA TGT GAA TGC-3' (SEQ ID NO: 3); Ex6: 5'-AAA TCA GTT CGA GGA AAG GGA AAG-3' (SEQ ID NO: 4);

Ex7: 5'-AAG CAT TTG TTT GTA CAA GAT G-3' (SEQ ID NO: 5). The Ex4 probe, designed according to the sequence within exon 4 of the VEGF gene, recognized transcripts of all 4 isoforms on Southern blotting. The Ex6 probe recognized transcripts corresponding to VEGF189 and 206, and the Ex7 probe hybridized to transcripts of the VEGF165, 189, and 206 isoforms. Hybridizations were carried out in 6xSSC/0.01% SDS and 10xDenhardts for 2 hours at 56° C. Blots were washed in 2xSSC/0.1% SDS for 2 hours, then exposed to Kodak X-Omat X ray film.

The Ex4 probe recognized three distinct bands, the Ex6 probe one band, and the Ex7 probe two bands. These results indicated that transcripts of VEGF121, 165, and 189 were present in THP-1 cells. A second larger band, presumably that corresponding to VEGF206, is occasionally recognized by the Ex6 probe. Importantly, the intensity of all bands is increased following addition of relaxin (100 ng/ml), indicating that relaxin stimulates VEGF production at the transcriptional level.

EXAMPLE 5

Second Messenger Pathways in VEGF Stimulation

Since relaxin causes an increase in cAMP in THP-1 cells, we investigated the potential role for this mediator in relaxin-induced VEGF secretion. Therefore, several different agents known to alter second messenger pathways were tested for their effect on VEGF secretion in THP-1 cells. For these experiments, forskolin, dbcAMP, dbcGMP and isobutylmethylxanthing (IBMX) were obtained from Sigma (St. Louis, Mo.). Cholera toxin, pertussis toxin, H-89, and bisindolylmalemide were purchased from Calbiochem (La Jolla, Calif.), and Ro, staurosporin, KT5720, and SQ22536 were obtained from Biomol (Plymouth Meeting, Pa.). The results of these experiments are shown below in Table I.

TABLE I

VEGF Regulation in THP-1 Cells

| Exp # | Agent | Dose | Net VEGF Expr pg/ml)* | (n)# |
|---|---|---|---|---|
| 1 | IBMX | $50 \times 10^{-6}$M | 154 ± 46 | (3) |
| 2 | IBMX | $50 \times 10^{-6}$M | 209 ± 20 | (3) |
|   | RLX | 10 ng/ml | 161 ± 19 | (3) |
|   | IBMX + RLX |  | 422 ± 37 | (3) |
| 3 | Ro | $500 \times 10^{-6}$M | 201.5 ± 97 | (3) |
| 3 | dbcAMP | $10^{-6}$M | 0 | (3) |
|   |  | $10^{-5}$M | 142 ± 26 | (3) |
|   |  | $10^{-4}$M | 488 ± 27 | (3) |
|   | dbcGMP | $10^{-6}$M – $10^{-4}$M | 0 | (3 each dose) |
| 4 | Cholera toxin | 1 $\mu$g/ml | 1278 ± 106 | (3) |
|   | Pertussis toxin | 1 $\mu$g/ml | 0 | (3) |
| 5 | PMA | 1 ng/ml | 342 ± 18 | (3) |

THP-1 cells were treated with agents for 8 h, except in Experiments 1, where the cells were treated for 24 h. Media were collected, and assayed for VEGF content by ELISA. Results are expressed as net VEGF expression calculated by subtracting the VEGF level expressed by the appropriate placebo-treated control group from the experimental group.
*Means = SEM, p 21 0.01 vs, placebo-treated group.
Numbers in parentheses indicate number of paired wells used to calculated mean differences.

Treatment of THP-1 cells with IBMX, a phosphodiesterase inhibitor, significantly increased their secretion of VEGF.

THP-1 cells treated with recombinant human relaxin (H2) (1 ng/ml) in the presence of IBMX secreted more VEGF than cells treated with either relaxin or IBMX alone. A more specific cAMP phosphodiesterase, Ro, also increased VEGF expression. Forskolin, a diterpene that stimulates adenyl cyclase, induced VEGF production a dose-dependent bi-phasic manner. Dibutyryl cAMP (at $10^{-6}$ M and $10^{-4}$ M), but not dibutyryl cGMP, also stimulated VEGF expression in a dose-dependant fashion. Cholera toxin, which elevates cAMP levels in these cells, stimulated VEGF expression while pertussis toxin did not.

Because previous experiments have suggested a role for Protein Kinase C in the induction of VEGF gene expression, we tested the ability of PMA to modulate VEGF production in THP-1 cells. PMA (1 ng/ml) significantly increased VEGF protein expression. However, at this same dose, PMA does not increase cAMP levels in these cells (data not shown).

Selective inhibitors of PKA and PKC were used to block VEGF induction by relaxin. PKA inhibitors (H-89, SQ22536, KT5720) used at or above their $K_1$ doses failed to completely inhibit VEGF stimulation, as measured by ELISA (data not shown). Furthermore, combining PKA and PKC inhibitors, KT5720 and bisindolylmaleimide respectively, did not inhibit the response over that of KF5720 alone.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A method of treating a condition amenable to treatment by promoting angiogenesis, the method comprising:

administering recombinant human relaxin (H2) to a patient at a predetermined rate so as to maintain a serum concentration of at least about 1 ng/ml;

continuing the administratior over a period sufficient to promote angiogenesis and treat the condition, wherein the condition is selected from the group consisting of an infection, and an ischemic wound.

2. The method of claim 1, wherein relaxin is administered from an osmotic pump.

3. The method of claim 2, wherein the osmotic pump is a multi-chamber osmotic pump system.

4. The method of claim 1, wherein the predetermined rate comprises sequentially timed dispensing from an osmotic pump.

5. The method of claim 1, wherein the administering is at a progressively diminishing rate.

6. A method of inducing secretion of vascular endothelial growth factor (VEGF) in a patient, comprising the steps of:

administering recombinant human relaxin (H2) to the patient, wherein the administering induces VEGF secretion, and wherein the relaxin is administered at a predetermined rate, so as to maintain a serum concentration of at least about 1 ng/ml of relaxin for at least 72 hours in the patient.

7. A method of inducing secretion of vascular endothelial growth factor (VEGF), comprising the steps of:

administering recombinant human relaxin (H2) to a patient wherein the administering is in a sufficient amount and over a sufficient period of time so as to induce VEGF secretion, wherein the administering is at a progressively diminishing rate.

* * * * *

SEQUENCE LISTING

<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
ccatgaactt tctgccct                                                    18

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
tgcatcgttc tgtatcagtc t                                                21

<210> SEQ ID NO 3
<211> LENGTH: 27
<212> TYPE: DNA
<213> ORGANISM: Artificial Sequence
<220> FEATURE:
<223> OTHER INFORMATION: probe

<400> SEQUENCE: 3
ttcctacagc acaacaaatg tgaatgc                                          27

<210> SEQ ID NO 4
<211> LENGTH: 24
<212> TYPE: DNA
<213> ORGANISM: Artificial Sequence
<220> FEATURE:
<223> OTHER INFORMATION: probe

<400> SEQUENCE: 4
aaatcagttc gaggaaaggg aaag                                             24

<210> SEQ ID NO 5
<211> LENGTH: 22
<212> TYPE: DNA

```
<213> ORGANISM: Artificial Sequence
<220> FEATURE:
<223> OTHER INFORMATION: probe

<400> SEQUENCE: 5
aagcatttgt ttgtacaaga tg                                              22
```